United States Patent [19]

Michaelson

[11] 4,347,232
[45] Aug. 31, 1982

[54] PREPARATION OF HYDROGEN PEROXIDE FROM ITS ELEMENTS

[75] Inventor: Robert C. Michaelson, Waldwick, N.J.

[73] Assignee: FMC Corporation, Philadelphia, Pa.

[21] Appl. No.: 274,597

[22] Filed: Jun. 17, 1981

[51] Int. Cl.³ ............................................. C01B 15/02
[52] U.S. Cl. ................................................... 423/584
[58] Field of Search ........................................ 423/584

[56] References Cited

U.S. PATENT DOCUMENTS

| | | | |
|---|---|---|---|
| 3,336,112 | 8/1967 | Hooper | 423/584 |
| 3,361,533 | 1/1968 | Hooper | 423/584 |
| 3,433,582 | 3/1969 | Campbell | 423/281 |
| 4,007,256 | 2/1977 | Kim et al. | 423/584 |
| 4,009,252 | 2/1977 | Izumi et al. | 423/584 |
| 4,128,627 | 12/1978 | Dyer et al. | 423/584 |
| 4,207,305 | 6/1980 | Diamond et al. | 423/584 |

FOREIGN PATENT DOCUMENTS 1094804 12/1967 United Kingdom .

OTHER PUBLICATIONS

Y. Takahashi et al, Chemical Communications, 1065–1066, (1970).
M. C. Mazza et al, Inorg. Chem. 12, 2955–2959, (1973).

Primary Examiner—Earl C. Thomas
Assistant Examiner—Wayne A. Langel
Attorney, Agent, or Firm—Richard E. Elden; Christopher Egolf

[57] ABSTRACT

Hydrogen peroxide is prepared by the homogeneously catalyzed reaction of hydrogen and oxygen in an inert organic solvent, by employing a palladium complex, selected from palladium(O) complexes of dibenzylidene acetone, as the catalyst.

8 Claims, No Drawings

PREPARATION OF HYDROGEN PEROXIDE FROM ITS ELEMENTS

BACKGROUND OF THE INVENTION

1. Field of the Invention

This invention relates to a process for preparing hydrogen peroxide from the homogeneously catalyzed reaction of hydrogen and oxygen.

2. Description of the Prior Art

Several methods are presently used to manufacture hydrogen peroxide on a commercial scale: (i) electrolysis of sulfate-containing solutions (e.g., ammonium bisulfate) to form persulfate which is hydrolyzed to recover the sulfate and produce hydrogen peroxide; (ii) oxidation of isopropyl alcohol to yield byproduct acetone and hydrogen peroxide; and (iii) autooxidation of anthraquinone to yield hydrogen peroxide. Disadvantages of these methods include the energy intensive nature of electrolysis processes, and the significant capital and raw material costs associated with the chemical processes.

As an alternative to these techniques, the direct chemical reaction of hydrogen and oxygen to form hydrogen peroxide has been investigated by a number of researchers.

U.S. Pat. No. 4,128,627 issued to Dyer et al discloses a homogeneous catalysis process for synthesizing hydrogen peroxide from hydrogen and oxygen, utilizing a water-insoluble catalyst in a two-phase reaction medium. Preferred catalysts in this homogeneous catalysis system are bis(tri(pentafluorophenyl)phosphine) palladium dichloride, bis(tricyclohexylphosphine) palladium dichloride and bis(triphenylarsine) palladium dichloride.

Processes for preparing hydrogen peroxide from its elements utilizing heterogeneous catalysis systems are disclosed in U.S. Pat. Nos. 4,009,252 issued to Izumi et al; 4,007,256 issued to Kim et al; 3,361,533 and 3,336,112 both issued to Hooper; 3,433,582 issued to Campbell and British Pat. No. 1,094,804 issued to Campbell.

None of these proposed direct synthesis methods, however, is known to have proven sufficiently efficient and satisfactory for preparing hydrogen peroxide on a commercial basis.

Catalysis systems for the preparation of hydrogen peroxide which employ homogeneous catalysis, i.e., catalyst dissolved in the reaction solvent, are preferred over heterogeneous catalysis i.e., solid phase catalyst, systems. Characteristics of homogeneous catalysis systems are generally mild reaction conditions (less energy intensive), high selectivity based on reactants (minimum reactant costs) and relatively high yields.

Despite such advantages, many prior art transition metal homogeneous catalysts suffer from drawbacks that are a deterrent to their commercial use. These adverse characteristics include poor catalyst stability under reaction conditions, limited catalyst solubility in the reaction medium, and low reaction rates for the production of hydrogen peroxide.

The homogeneous catalysts of the present invention are intended to minimize the negative characteristics ordinarily associated with homogeneous catalysis systems.

SUMMARY OF THE INVENTION

In accordance with the present invention, hydrogen peroxide is produced by the catalyzed reaction of hydrogen and oxygen by contacting gaseous hydrogen and oxygen with a two phase homogeneous catalysis system, which contains (i) an inert organic solvent phase having dissolved therein as the homogeneous catalyst a palladium(O) complex of dibenzylidene acetone and (ii) an aqueous solution as the second phase, for sufficient time to form hydrogen peroxide; extracting hydrogen peroxide reaction product from the organic phase into the aqueous phase; and recovering the aqueous phase containing hydrogen peroxide.

DETAILED DESCRIPTION

The homogeneous catalysts employed in the production of hydrogen peroxide according to the invention are palladium-(O) complexes of dibenzylidene acetone. Dibenzylidene acetone may also be designated as 1,5-diphenyl-1,4-pentadien-3-one, or abbreviated as DBA, and both the informal and proper chemical terms are used interchangeably in this disclosure to refer to the same compound, having the general formula

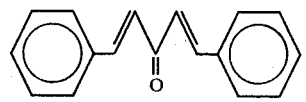

The palladium is zero valent in these dibenzylidene acetone complexes and may also be combined with the dibenzylidene acetone in other than a 1:1 ratio. Palladium(O) complexes of unsubstituted dibenzylidene acetone, for example, include bis-1,5-diphenyl-1,4-pentadien-3-one palladium(O); tris-1,5-diphenyl-1,4-pentadien-3-one palladium(O); and tris-1,5-diphenyl-1,4-pentadien-3-one dipalladium(O). Reference to a "palladium(O) complex of dibenzylidene acetone" is intended to encompass the individual complexes, as well as their mixtures.

The dibenzylidene acetone moiety of the palladium(O) complexes of dibenzylidene acetone, may be substituted, as well as unsubstituted. Preferred substituents are halogens, particularly chlorine and fluorine, lower alkyl groups, particularly methyl, ethyl and propyl, and lower alkoxy groups, particularly methoxy.

Good catalytic activity has been obtained when the substituents are located in the para-position on the benzene rings of the dibenzylidene acetone. Preferred as substituted catalysts include palladium(O) complexes of p-chloro, p-fluoro, p-isopropyl- and p-methoxy-substituted dibenzylidene acetone.

An advantage of the substituted dibenzylidene acetone palladium(O) complexes (particularly the halo-substituted complexes) is their excellent stability against loss of catalytic activity at temperatures around 25° C. This good catalyst stability allows the use of long reaction times, if desired, and permits the catalyst to be employed for longer periods without need for regeneration or replacement.

Another advantageous property associated with the substituted dibenzylidene acetone palladium(O) complexes (particularly with lower alkyl, e.g., isopropyl, substituents) is their improved solubility in the inert organic solvent. The better solubility allows a higher concentration of catalyst to be employed in the solvent, which can provide an enhanced yield or reaction rate for hydrogen peroxide formation.

Concentration of the catalysts employed in the inert organic solvent in this invention may range from as low as about $5. \times 10^{-5}$ M (g-moles catalyst/liter of organic solvent) up to a saturation concentration in the organic solvent. The catalyst is preferably present in the organic solvent at concentrations of $0.1 \times 10^{-3}$ M up to saturation and most preferably, $0.5 \times 10^{-3}$ M to $2.5 \times 10^{-3}$ M.

The preferred catalysts, when utilized in the homogeneous catalysis system of this invention, are capable of producing hydrogen peroxide concentrations of over 1.5 wt % $H_2O_2$ in the aqueous phase of a two phase (inert organic solvent mixed with water) system.

The reaction is performed by employing a two-phase reaction medium which consists of an organic solvent phase and an aqueous phase.

The catalysts of the invention are substantially insoluble in water, so the organic solvent must be capable of dissolving the catalysts and should also be immiscible with water. The organic solvent must be inert, i.e., non-reactive with hydrogen peroxide under the reaction conditions.

The aqueous phase is employed in the reaction medium to extract the hydrogen peroxide reaction product from the catalyst-containing organic phase, so as to minimize the possibility of catalyst-induced peroxide decomposition. Consequently, the organic solvent should have a distribution coefficient with respect to hydrogen peroxide that favors the removal of hydrogen peroxide from the organic phase to the aqueous phase, thus enhancing the aqueous extraction of hydrogen peroxide. Additives to promote the distribution of hydrogen peroxide to the aqueous phase may be present in the aqueous phase but are not necessary.

Preferred organic solvents include toluene, xylene, and chlorinated solvents like dichloromethane, chlorobenzene, and dichlorobenzene; toluene is most preferred.

The ratio of the organic solvent phase to aqueous phase is not critical; it may range from about 1:9 to 9:1 by volume. Volume ratios of solvent phase: aqueous phase in excess of 1:1 are preferred, the ratio being selected so as to maximize hydrogen peroxide concentration in the aqueous phase without significantly reducing the total amount of peroxide produced.

The two phases should be maintained in good contact during the reaction. This may be accomplished via mechanical agitation or, more preferably, by bubbling or similarly contacting the gaseous hydrogen and oxygen reactants with the two liquid phases. Upon completion of the reaction the two liquid phases may simply be allowed to separate, and the $H_2O_2$-containing aqueous phase readily recovered.

The gaseous reactants, hydrogen and oxygen, may be employed as pure gases or mixed with other gases that are inert with respect to the peroxide reaction. The oxygen, for example, may be supplied as air or other inert diluent or carrier gases may also be used.

The volumetric ratio of hydrogen to oxygen in the gaseous atmosphere in contact with the catalyst-containing inert organic solvent may vary within wide limits. Equimolar amounts of hydrogen and oxygen give satisfactory results. However, an oxygen-rich atmosphere may be desirable under some circumstances for minimizing adverse side reactions, such as reduction of the hydrogen peroxide product to water. Since hydrogen is generally less soluble in organic solvents than oxygen, a hydrogen-rich atmosphere may be advantageous so that essentially all oxygen is absorbed, permitting recycle of a substantially pure hydrogen atmosphere.

For obvious reasons, mixtures of hydrogen and oxygen which are outside of the explosive region for $H_2$-$O_2$ mixtures are clearly desirable.

The temperature at which the hydrogen peroxide reaction is carried out may range from the freezing point of the aqueous phase up to 35° C. or above. Temperatures around 0° C.–25° C., are preferred. The lower temperatures, 0° C. or less, enhance catalyst stability, albeit at the expense of a slow reaction rate of peroxide formation. Temperatures above 35° C. provide rapid formation of hydrogen peroxide but catalyst activity may be short-lived.

The reaction process is desirably performed at superatmospheric pressure, up to about 25,000 kPa. Moderate pressures of about 500 to 3500 kPa (50–500 psig) are preferred. Higher pressures would be anticipated to provide an increased rate of formation of hydrogen peroxide in the reaction medium, but such higher pressures are more difficult and expensive to maintain on a commercial scale.

Reaction times may range from a few minutes to several hours. Preferred reaction times are from 0.25 hour to 24 hours. The optimal choice of reaction time employed is typically dependent, in part, on the reaction temperature and particular catalyst utilized, since both the rate of hydrogen peroxide formation and catalyst stability are affected by reaction temperature.

Catalyst Preparation

The synthesis of the palladium complexes of dibenzylidene acetone utilized in the process of this invention is relatively straightforward, as described below.

The catalyst was typically prepared by reducing sodium chloropalladite or palladium dichloride in a methanol solution in the presence of an excess of the appropriate ligand, e.g., dibenzylidene acetone.

Bis-(dibenzylidene acetone) palladium(O)

Sodium chloropalladite was first synthesized by dissolving palladium dichloride (1.0 g; 5.64 mmole) in concentrated hydrochloric acid (100 ml), adding excess sodium chloride (1.0 g; 17.1 mmole), and then evaporating the solution under vacuum. A mixture of the sodium chloropalladite (2.0 g; 6.80 mmole) and excess dibenzylidene acetone (6.37 g; 27.2 mmole) was refluxed in methanol (200 ml) under an inert atmosphere. Sodium acetate (1.67 g; 20.4 mmole), which served as a proton acceptor, was added to the hot solution. The solution was then cooled in an ice bath to precipitate the purple crystals of bis-(dibenzylidene acetone) palladium(O), which were filtered and dried.

This synthesis technique is generally that described by Takahashi et al in *Chem. Commun.* 1065 (1970).

Tris-(dibenzylidene acetone) palladium(O)

Bis-(dibenzylidene acetone) palladium (0.10 g; 0.17 mmole) was dissolved in methylene chloride (100 ml), and the solution filtered on a millepore filter to remove elemental palladium. Dibenzylidene acetone (0.51 mmole) was added to the solution, and the solution was stirred for 24 hours at ambient temperature. The solution was then evaporated to yield purple crystals of the tris-(dibenzylidene acetone) palladium product.

Tris-(dibenzylidene acetone) dipalladium(O)

Dibenzylidene acetone (4.6 g; 19.6 mmole) and sodium acetate (3.9 g; 47.5 mmole) were dissolved in methanol (150 ml) by heating under reflux, under an inert atmosphere. Palladium dichloride (1.05 g; 5.92 mmole) was added to the hot solution, which was stirred and refluxed for four hours. Purple crystals of tris-(dibenzylidene acetone) dipalladium were precipitated by cooling the solution and were filtered and dried.

$\mu_3$-Tris-(1,5-di(p-methoxyphenyl)-1,4-pentadien-3-one) dipalladium(O)

p-Methoxybenzaldehyde (136.4 g; 1.0 mole) was dissolved in acetone (29.0 g; 0.5 mole). Half of this solution was added, at ambient temperature, to a solution of sodium hydroxide (100 g), water (1 l), and ethanol (800 ml), and the mixture was stirred vigorously for 15 minutes. The remaining p-methoxybenzaldehyde solution was added, and the mixture was stirred for 30 minutes. Yellow-green crystals were filtered from the mixture, waterwashed, dissolved in ether, precipitated and filtered, waterwashed and the yellow crystals of 1,5-di(p-methoxyphenyl)-1,4-pentadien-3-one dried under vacuum.

This precursor (5.8 g; 20 mmole) and sodium acetate (3.9 g) were dissolved in methanol (300 ml) at a temperature of 50° C. To the solution was added $PdCl_2$ (1.05 g; 6 mmole), the temperature reduced to 40° C., and the solution stirred for four hours. The solution was then cooled to precipitate purple crystals of tris-(1,5-di(p-methoxyphenyl)-1,4-pentadien-3-one) dipalladium(O), which were filtered, washed with water and acetone, and dried under vacuum.

$\mu_3$-Tris-(1,5-di(p-isopropylphenyl)-1,4-pentadien-3-one) palladium(O)

The catalyst was prepared via an intermediate, 1,5-di(p-isopropylphenyl)-1,4-pentadien-3-one, which was obtained as follows. p-Isopropylbenzaldehyde (149.4 g, 1.0 mole) was dissolved in acetone (29.5 g, 0.5 mole). Half of the solution was added at ambient temperature to a second solution of sodium hydroxide (100.5 g), water (1.0 l), and ethanol (800 ml). The combined solutions were stirred vigorously for 15 minutes, the remaining p-isopropylbenzaldehyde solution was added, and the combined solution stirred for 30 minutes at ambient temperature. The intermediate, 1,5-di(p-isopropylphenyl)-1,4-pentadien-3-one, was recovered from the solution as a yellow oil.

1,5-Di(p-isopropylphenyl)-1,4-pentadiene-3-one (6.0 g, 20 mmole) and sodium acetate (3.9 g) were dissolved in methanol (200 ml) at a temperature of 50° C. Palladium dichloride (1.05 g, 6 mmole) was added to the hot solution, the temperature was reduced to 40° C., and the mixture was stirred for 4 hours. The $\mu_3$-tris(1,5-di(p-isopropylphenyl)-1,4-pentadien-3-one) palladium(O) was a purple precipitate, which was filtered from the cold solution, washed with water and acetone, and dried under vacuum.

$\mu_3$-Tris-(1,5-di(p-chlorophenyl)-1,4-pentadien-3-one) dipalladium(O)

The catalyst was prepared via an intermediate, 1,5-di(p-chlorophenyl)-1,4-pentadien-3-one, which was obtained as follows: p-Chlorobenzaldehyde (149.05 g, 0.1 mole) and acetone (2.9 g, 0.05 mole) were dissolved in ethanol (40 ml). Half of the solution was added at ambient temperature to a solution of sodium hydroxide (10.0 g), water (100 ml) and ethanol (40 ml). The combined solutions were stirred vigorously for 15 minutes, the remaining p-chlorobenzaldehyde solution was added, and the combined solution stirred for 30 minutes at ambient temperature. The intermediate, 1,5-di(p-chlorophenyl)-1,4-pentadien-3-one, was recovered from the solution as a yellow solid.

1,5-Di(p-chlorophenyl)-1,4-pentadiene-3-one (6.0 g, 20 mmole) and sodium acetate (3.9 g) were dissolved in a mixture of 2-propanol (400 ml), methanol (200 ml), and ethyl acetate (200 ml) at a temperature of 70° C. Palladium dichloride (1.05 g, 6 mmole) was added to the hot solution, the temperature was reduced to 40° C., and the mixture was stirred for 4 hours. The $\mu_3$-tris(1,5-di(p-chlorophenyl)-1,4-pentadien-3-one) dipalladium(O) was a purple precipitate, which was filtered from the hot solution, washed with water and acetone, and dried under vacuum.

Catalyst Evaluation Procedure

The palladium catalysts employed in the method of this invention were evaluated by the following procedure.

The reaction of hydrogen and oxygen to produce hydrogen peroxide was performed in a 500 ml heavy walled Fisher-Porter glass pressure bottle, which was fitted with a "Christmas tree" head that contained a pressure gauge, inlet system for two gases, a vent or auxiliary inlet, and an O-ring closure to the bottle.

The reaction bottle was typically charged with 40 mg of solid palladium catalyst, 40 ml of solvent, in which the catalyst dissolved, and 40 ml of water. The bottle was sealed and charged with equal parts of hydrogen and oxygen gas to a total pressure of 150 psig (1034 kPa).

The contents of the reaction bottle were vigorously agitated via a magnetic stirrer bar present in the bottle. Temperature of the bottle contents was controlled via ice or water bath.

After the desired reaction time had elapsed, the reaction bottle was vented to the atmosphere and its contents analyzed for hydrogen peroxide (by permanganate or ceric sulfate titration).

EXAMPLE 1

A mixture of dibenzylidene acetone complexes of palladium (Pd(DBA)$_2$; Pd(DBA)$_3$; and Pd$_2$(DBA)$_3$) was utilized in Examples 1, 2 and 3.

The dibenzylidene acetone palladium catalyst (40.2 mg; $7.0 \times 10^{-2}$ mmole) was dissolved in 40 ml of toluene, to which 40 ml of water had been added, all contained in a 500 ml glass reaction bottle. The bottle was pressurized to 140 psig (965 kPa) with equal volumes of hydrogen and oxygen gas. The sealed reaction bottle was maintained at a temperature of 0° C., and its contents vigorously agitated for six hours.

The reaction bottle was then vented, and its contents analyzed for hydrogen peroxide. The aqueous phase was found to contain 0.74 wt % $H_2O_2$.

EXAMPLE 2

The procedure of Example 1 was again followed, with essentially the same amount of catalyst (42.0 mg; $7.3 \times 10^{-2}$ mmole) being employed. Instead of the reaction temperature of 0° C., the temperature of the reaction bottle contents was maintained at 25° C., and the bottle contents were agitated for a slightly longer period, eight hours. When the aqueous phase was analyzed, it was found to contain 0.30 wt % $H_2O_2$.

EXAMPLE 3

The general procedure of Example 1 was again followed, with a different solvent, chlorobenzene (40 ml), being substituted for the toluene. A similar amount (40.1 mg; $7.0 \times 10^{-2}$ mmole) of catalyst was employed.

The reactor bottle contents were maintained at a temperature of 5° C., with agitation, for a relatively short time, one hour. When the aqueous phase was analyzed, it was found to contain 0.82 wt % $H_2O_2$.

EXAMPLE 4

In lieu of the unsubstituted dibenzylidene acetone palladium catalyst of Examples 1 to 3, tris-(1,5-di(p-chlorophenyl)-1,4-pentadiene-3-one) dipalladium(O) was utilized in Examples 4 to 6.

The tris-(1,5-di(p-chlorophenyl)-1,4-pentadien-3-one)-dipalladium-(O) catalyst (40 mg; $3.6 \times 10^{-2}$ mmole) was dissolved in 40 ml of chlorobenzene and, along with 40 ml of water, was introduced into the glass reaction bottle. The bottle was pressurized to 150 psig (1034 kPa) with equal volumes of hydrogen and oxygen gas.

The reactor bottle contents were maintained at a temperature of 25° C., with agitation, for a period of two hours. When the aqueous phase was analyzed, it was found to contain 1.7 wt % $H_2O_2$.

EXAMPLE 5

The procedure of Example 4 was again followed, except that toluene (40 ml) was substituted for the chlorobenzene solvent.

The reactor bottle was charged with equal volumes of hydrogen gas to a pressure of 150 psig (1040 kPa) and maintained at 25° C., with agitation, for two hours. When the aqueous phase was analyzed, it was found to contain 0.61 wt % $H_2O_2$.

EXAMPLE 6

Example 5 was essentially repeated, except that the reactor bottle contents were agitated, at a temperature of 25° C., for six hours instead of the previous two hours.

When the aqueous phase was analyzed, it was found to contain a peroxide concentration, 1.28 wt % $H_2O_2$, that was twice that of Example 5.

EXAMPLE 7

The procedure of Example 1 was essentially followed, except that $\mu_3$-tris-(1,5-di(p-isopropylphenyl)-1,4-pentadien-3-one) palladium(O) was employed as the catalyst.

The reactor bottle contents were maintained at a low temperature, 5° C., with agitation, for a period of four hours.

When the aqueous phase was analyzed it was found to contain 0.45 wt % $H_2O_2$.

I claim:

1. In a process for producing hydrogen peroxide by the catalyzed reaction of hydrogen and oxygen, the improvement which comprises contacting gaseous hydrogen and oxygen with a two phase homogeneous catalysis system, which contains (i) an inert organic solvent phase having dissolved therein as the homogeneous catalyst a palladium(O) complex of dibenzylidene acetone and (ii) an aqueous solution as the second phase, for sufficient time to form hydrogen peroxide; extracting hydrogen peroxide reaction product from the organic phase into the aqueous phase; and recovering the aqueous phase containing hydrogen peroxide.

2. The process of claim 1 wherein the benzene rings of the benzylidene acetone are unsubstituted or substituted with halogen, lower alkyl or lower alkoxy groups.

3. The process of claim 2 wherein the palladium(O) complex of dibenzylidene acetone is selected from the group consisting of palladium(O) complexes of 1,5-diphenyl-1,4-pentadien-3-one; palladium(O) complexes of 1,5-di(p-chlorophenyl)-1,4-pentadien-3-one; palladium(O) complexes of 1,5-di(p-fluorophenyl)-1,4-pentadien-3-one; palladium-(O) complexes of 1,5-di(p-isopropylphenyl)-1,4-pentadien-3-one; and palladium(O) complexes of 1,5-di(p-methoxyphenyl-1,4-pentadien-3-one.

4. The process of claim 1 wherein the catalyst is employed in amounts of from $1 \times 10^{-4}$ gram-moles/liter of solvent up to a saturation concentration in the organic solvent.

5. The process of claim 1 wherein the inert organic solvent is selected from the group consisting of toluene, xylene, chlorobenzene, dichlorobenzene and dichloromethane.

6. The process of claim 1 wherein the relative amounts of inert organic solvent and aqueous phase are such as to provide a volume ratio of from 1:9 to 9:1.

7. The process of claim 1 wherein the reaction is performed at a temperature of from about 0° C. to about 35° C.

8. The process of claim 1 wherein the reaction time is from 0.25 to 24 hours.

* * * * *